United States Patent
Dwyer

(10) Patent No.: US 10,434,160 B2
(45) Date of Patent: Oct. 8, 2019

(54) CYCLOPHOSPHAMIDE ANALOGS FOR USE AS IMMUNOGENS AND ASSAY CONJUGATES FOR AN IMMUNOASSAY OF CYCLOPHOSPHAMIDE AND IFOSFAMIDE

(71) Applicant: Becton, Dickinson and Company, Franklin Lakes, NJ (US)

(72) Inventor: Brian P. Dwyer, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/757,854

(22) PCT Filed: Sep. 7, 2016

(86) PCT No.: PCT/US2016/050495
§ 371 (c)(1),
(2) Date: Mar. 6, 2018

(87) PCT Pub. No.: WO2017/044453
PCT Pub. Date: Mar. 16, 2017

(65) Prior Publication Data
US 2018/0326031 A1 Nov. 15, 2018

Related U.S. Application Data

(60) Provisional application No. 62/216,943, filed on Sep. 10, 2015.

(51) Int. Cl.
| | | |
|---|---|---|
| *A61K 39/00* | (2006.01) | |
| *C07F 9/6584* | (2006.01) | |
| *G01N 33/94* | (2006.01) | |
| *A61K 47/68* | (2017.01) | |
| *A61K 47/54* | (2017.01) | |
| *C07K 16/06* | (2006.01) | |
| *C12N 5/16* | (2006.01) | |
| *G01N 33/531* | (2006.01) | |

(52) U.S. Cl.
CPC ........ *A61K 39/0013* (2013.01); *A61K 47/555* (2017.08); *A61K 47/6843* (2017.08); *A61K 47/6897* (2017.08); *C07F 9/65846* (2013.01); *C07K 16/065* (2013.01); *C12N 5/163* (2013.01); *G01N 33/531* (2013.01); *G01N 33/94* (2013.01); *G01N 33/9493* (2013.01)

(58) Field of Classification Search
None
See application file for complete search history.

(56) References Cited

U.S. PATENT DOCUMENTS

| 6,156,878 A | 12/2000 | Godfrey et al. |
| 7,276,347 B2 | 10/2007 | Salamone et al. |
| 2012/0148611 A1 | 6/2012 | Brodsky et al. |

FOREIGN PATENT DOCUMENTS

| WO | WO 1991/17271 | 11/1991 |
| WO | WO 1992/01047 | 1/1992 |
| WO | WO 1997/22614 | 6/1997 |
| WO | WO 2000/052015 | 9/2000 |
| WO | WO 2006/020263 | 2/2006 |
| WO | WO 2010/002883 | 1/2010 |
| WO | WO 2010/085377 | 7/2010 |
| WO | WO 2014/001967 | 1/2014 |
| WO | WO 2014/202791 | 12/2014 |

OTHER PUBLICATIONS

Bakke et al., J. Agr. Food Chem., vol. 20, No. 2, 1972 (Year: 1972).*
Binotto et al., Ifosfamide and Cyclophosphamide: effects on immunosurveillance. Oncology (2003) 65(Suppl 2):17-20.
Cox et al., The Use of Cyclophosphamide analogs in mechanistic studies of the metabolism of cyclophosphamide, Proceedings of the $2^{nd}$ Inter'l Symposium on Mass Spectrometry in Biochemistry and Medicine, Mario Negri Institute for Pharmacological Research, Jun. 1974; Spectrum Publications (1976) 1:59-71.
Ludeman et al., The Chemistry of the Metabolites of cyclophosphamide. Curr Pharm Des. (1999) 5(8):627-643.
European Extended Search Report dated Jan. 7, 2019 for EP Application No. 16844955.1, filed Feb. 23, 2018.
Chothia et al., (1987), Canonical Structures for the Hypervariable Regions of Immunoglobulins, J Mol Biol. 196:901-917.
Harlow et al.,[Eds.] *Antibodies, A Laboratory Manual* Second Edition (C.S.H.P. NY, 2014); Table of Contents in 22 pages.
Huse et al., (1989) Generation of a Large Combinatorial Library of the Immunoglobulin Repertoire in Phage Lambda, Science 246:1275-1281.
Kabat et al., [Eds.] *Sequences of Proteins of Immunological Interest*, U.S. Department of Health and Human Services; $5^{th}$ Edition, (1991) in two Volumes; Table of Contents in 28 pages.

(Continued)

*Primary Examiner* — Karl J Puttlitz
(74) *Attorney, Agent, or Firm* — Knobbe, Martens, Olson & Bear, LLP

(57) ABSTRACT

The present application relates to antibodies that bind to small molecules such as cyclophosphamide, ifosfamide, and analogs thereof, and immunological assays for determining the presence and/or quantifying the amount of cyclophosphamide and/or ifosfamide in a sample. By way of example, such immunological assays can be used for environmental testing.

19 Claims, No Drawings

(56) References Cited

OTHER PUBLICATIONS

Paul, [Eds.], *Fundamental Immunology* (Raven Press, 2d ed., 1989); Table of Contents in 6 pages.
Roitt et al., [Eds.] *Immunology* (2d ed. 1989), Chapter 6 in 14 pages.
International Search Report and Written Opinion dated Nov. 3, 2016 for PCT Application No. PCT/US2016/50495, filed Sep. 7, 2016.

* cited by examiner

CYCLOPHOSPHAMIDE ANALOGS FOR USE AS IMMUNOGENS AND ASSAY CONJUGATES FOR AN IMMUNOASSAY OF CYCLOPHOSPHAMIDE AND IFOSFAMIDE

CROSS-REFERENCE TO RELATED APPLICATIONS

The present application is the U.S. National Phase of PCT Application No. PCT/US2016/050495, filed Sep. 7, 2016, which claims the benefit of U.S. Provisional App. No. 62/216,943, filed Sep. 10, 2015, the entirety of which is hereby incorporated by reference.

FIELD

The present application relates to the field of antibodies that bind to small molecules such as cyclophosphamide, ifosfamide, and analogs thereof, and immunological assays for determining the presence and/or quantifying the amount of cyclophosphamide and/or ifosfamide in a sample. By way of example, such antibodies and/or immunological assays can be used for environmental testing.

BACKGROUND

Cyclophosphamide is a prodrug of a nitrogen mustard alkylating agent, in which the reactivity of the bis(2-chloroethyl)amino group is attenuated. Upon oxidation in vivo the six-membered ring opens, enhancing the reactivity of the nitrogen mustard, which then acts to cross-link DNA. Cyclophosphamide has severe and life-threatening adverse effects, including acute myeloid leukemia, bladder cancer, hemorrhagic cystitis, and permanent infertility, especially at higher doses. Ifosfamide is also a nitrogen mustard alkylating agent used in the treatment of cancer. Ifosfamide can cause encephalopathy, affects peripheral nerves, and interfere with neurological development in children.

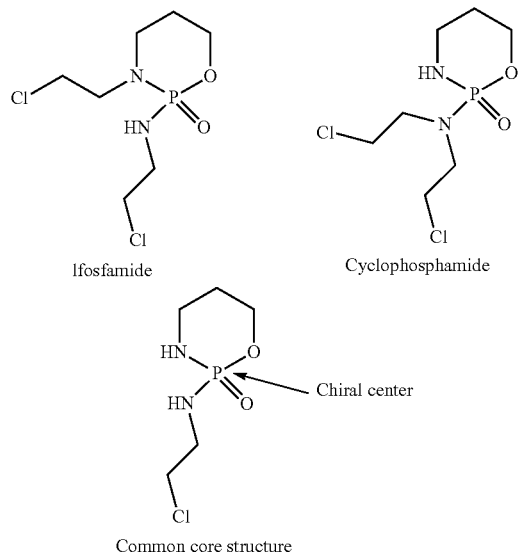

So far, there is no commercial immunoassay kit for the detection of cyclophosphamide or ifosfamide. Additionally there are no commercially available antibodies against cyclophosphamide or ifosfamide. Therefore, there exists a need for developing immunoassays for these cytotoxic agents.

SUMMARY

Embodiments of the present application are directed to a family of cyclophosphamide analogs that may be used as immunogens for generating antibodies that recognize cyclophosphamide and/or ifosfamide. These cyclophosphamide analogs can also be used to generate assay conjugates that can be used in an immunoassay for detection of cyclophosphamide and/or ifosfamide. Each of the analogs contains the functional groups for the purpose of conjugation but maintain the six-membered ring as an important epitope for antibody generation and drug recognition.

Some embodiments of the present application are directed to cyclophosphamide analogs comprising a structure of Formula (I) or (II):

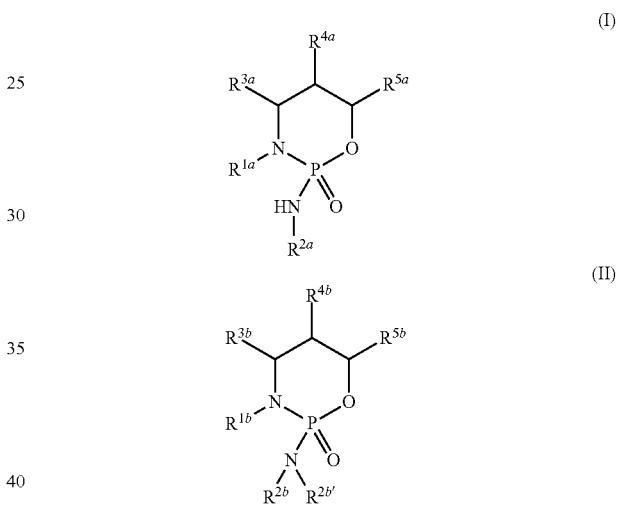

where $R^{1a}$ is selected from hydrogen or $-(CH_2)_m-X$; $R^{2a}$ is $-(CH_2)_n-Y$; $R^{1b}$ is $-(CH_2)_m-X$; each of $R^{2b}$ and $R^{2b'}$ is independently selected from $-(CH_2)_k-Z$; each $R^{3a}$, $R^{4a}$, $R^{5a}$, $R^{3b}$, $R^{4b}$ and $R^{5b}$ is independently selected from hydrogen, halogen, hydroxy, amino, cyano, $C_1$-$C_6$ alkyl, $C_2$-$C_6$ alkenyl, $C_2$-$C_6$ alkynyl, $C_3$-$C_7$ cycloalkyl, 5-10 membered heterocyclyl, aryl, aralkyl, 5-10 membered heteroaryl, $C_1$-$C_6$ alkoxy, $C_1$-$C_6$ alkoxy($C_1$-$C_6$)alkyl, aryloxy, halo($C_1$-$C_6$)alkyl, halo($C_1$-$C_6$)alkoxy, $C_1$-$C_6$ alkylthio, arylthio, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, and oxo (=O); X is a functional group selected from amine, thiol, carboxylic acid, hydrazide, hydrazine, oxime, or hydroxylamine; Y is a functional group independently selected from halogen, hydroxy, amine, thiol, carboxylic acid, hydrazide, hydrazine, oxime, or hydroxylamine; Z is selected from halogen or hydroxy; and each m, n and k is independently an integer from 2 to 10.

In some embodiments of the compounds of Formula (I), $R^{1a}$ is hydrogen and $R^{2a}$ is $-(CH_2)_n-Y$, wherein Y is selected from a functional group that is capable of forming conjugate with a carrier protein, for example, amine, thiol, carboxylic acid, hydrazide, hydrazine, oxime, or hydroxylamine. In some such embodiments, Y is selected from thiol or carboxylic acid. In some such embodiments, n is an integer of 2.

In some alternative embodiments of the compounds of Formula (I), $R^{1a}$ is —$(CH_2)_m$—X wherein X is selected from a functional group that is capable of forming conjugate with a carrier protein, for example, amine, thiol, carboxylic acid, hydrazide, hydrazine, oxime, or hydroxylamine. In some such embodiments, X is selected from thiol or carboxylic acid. In some such embodiments, $R^{2a}$ is —$(CH_2)_n$—Y, where Y is selected from halogen (e.g., chloro) or hydroxy. In some such embodiments, m is an integer of 3 and n is an integer of 2.

In some embodiments of the compounds of Formula (II), $R^{1b}$ is —$(CH_2)_m$—X wherein X is selected from a functional group that is capable of forming conjugate with a carrier protein, for example, amine, thiol, carboxylic acid, hydrazide, hydrazine, oxime, or hydroxylamine. In some such embodiments, X is selected from thiol or carboxylic acid. In some such embodiments, each $R^{2b}$ and $R^{2b'}$ is —$(CH_2)_k$—Z and Z is selected from halogen (e.g., chloro) or hydroxy. In some such embodiments, m is an integer of 2. In some embodiments, at least one k is an integer of 2. In some further embodiments, both k is an integer of 2.

In some embodiments, at least one of $R^{3a}$, $R^{4a}$, $R^{5a}$ of Formula (I) and at least one of $R^{3b}$, $R^{4b}$, $R^{5b}$ of Formula (II) is hydrogen. In some further embodiments, each $R^{3a}$, $R^{4a}$, $R^{5a}$ of Formula (I) and $R^{3b}$, $R^{4b}$, $R^{5b}$ of Formula (II) is hydrogen.

Some embodiments of the present application are directed to an immunogen comprising a cyclophosphamide analog as described herein covalently bonded to an immunogenic polymer or carrier through the functional groups X or Y of the analog compound. In some embodiments, the immunogenic polymer or carrier is selected from an immunologically active protein or polypeptide.

Some embodiments of the present application are directed to an antibody which substantially selectively binds to cyclophosphamide, ifosfamide, or cyclophosphamide and ifosfamid. In some embodiments, the antibody is derived from an immunogen described herein. As such, in some embodiments, the antibody binds to cyclophosphamide, ifosfamide, or cyclophosphamide and ifosfamide, and further binds to a compound of Formula (I), in which a carrier is covalently bound to either X or Y, and in which the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle. In some embodiments, the antibody binds to cyclophosphamide, ifosfamide, or cyclophosphamide and ifosfamide, and further binds to a compound of Formula (II), in which a carrier is covalently bound to X, in which the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle. In some embodiments, the antibody binds to cyclophosphamide and the carrier comprises KLH. In some embodiments, the antibody binds to ifosfamide and the carrier comprises KLH. In some embodiments, the antibody comprises a monoclonal antibody. In some embodiments, the antibody binds to cyclophosphamide and ifosfamide, and the carrier comprises KLH. In some embodiments, the antibody comprises a polyclonal antibody.

Some embodiments of the present application are directed to an immunoassay for detecting the presence of cyclophosphamide and/or ifosfamide in a sample, comprising an assay conjugate, where the assay conjugate comprises a cyclophosphamide analog as described herein covalently bonded to a carrier through the functional groups X or Y of the analog compound. In some embodiments, the carrier is selected from a protein or polypeptide. In some embodiments, the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle.

Some embodiments of the present application are directed to a kit comprising reagents for detecting the presence of cyclophosphamide and/or ifosfamide in a sample, one of the reagents being a conjugate of a carrier covalently bonded to a cyclophosphamide analog as described herein through the functional groups X or Y of the analog compound. In some embodiments, the carrier is selected from a protein or polypeptide. In some embodiments, the kit further comprises an antibody as described herein. In some embodiments, the antibody binds to cyclophosphamide and/or ifosfamide as described herein.

In some embodiments, a cyclophosphamide analog as described herein further comprises a carrier covalently bound to X, wherein the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle. In some embodiments, a cyclophosphamide analog as described herein further comprises a carrier covalently bound to Y, wherein the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle.

Some embodiments of the present application are directed to an antibody that binds specifically to a cyclophosphamide analog as described herein, for example a cyclophosphamide analog further comprising a carrier covalently bound to X, and/or further comprising a carrier bound to Y as described herein. In some embodiments, the antibody binds to a cyclic cyclophosphamide with a dissociation constant ($K_d$) that is numerically less than 1/10 the dissociation constant for acyclic cyclophosphamide of formula (III). In some embodiments, the antibody binds to a cyclic cyclophosphamide with a dissociation constant (Kd) that is numerically less than 1/1000 the dissociation constant for acyclic cyclophosphamide of formula (III). In some embodiments, the antibody comprises a monoclonal antibody. In some embodiments, the antibody comprises a polyclonal antibody.

Some embodiments of the present application are directed to methods of making an antibody that binds specifically to cyclophosphamide. The method can comprise administering to a host organism, an immunogen as described herein or a compound of Formula (I) (in which a carrier is covalently bound to X or Y, in which the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle), or a compound of Formula (II) (in which a carrier is covalently bound to X, in which the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle). In some embodiments, the carrier comprises KLH. The method can comprise isolating antibody-producing cells or antibodies from the host organism. The method can comprise screening antibodies derived from the antibody-producing cells or the antibodies from the host organism for affinity to cyclophosphamide. In some embodiments, the host organism comprises a mouse, rat, hamster, guinea pig, rabbit, donkey, or goat. In some embodiments, the carrier comprises KLH. In some embodiments, the antibody-producing cells are isolated, and antibodies derived from the antibody-producing cells are screened for affinity to cyclophosphamide, and the antibody that binds specifically to cyclophosphamide is monoclonal. In some embodiments, the method further comprises constructing hybridomas from the isolated antibody-producing cells. In some embodiments, the method further comprises screening nucleic acids from the isolated antibody-producing cells by phage display. In some embodiments, the method further comprises screening for antibodies that bind specifically to cyclophosphamide compared to an acyclic metabolite of formula (III). In some embodiments, the antibodies from the host organism are screened for affinity to cyclophosphamide, and the antibody that binds specifically to cyclophosphamide is polyclonal.

Some embodiments of the present application are directed to methods of making an antibody that binds specifically to ifosfamide. The method can comprise administering to a host organism, an immunogen as described herein or a compound of Formula (I) (in which a carrier is covalently bound to X or Y, in which the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle), or a compound of Formula (II) (in which a carrier is covalently bound to X, in which the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle). In some embodiments, the carrier comprises KLH. The method can comprise isolating antibody-producing cells or antibodies from the host organism. The method can comprise screening antibodies derived from the antibody-producing cells or the antibodies from the host organism for affinity to ifosfamide. In some embodiments, the host organism comprises a mouse, rat, hamster, guinea pig, rabbit, donkey, or goat. In some embodiments, the carrier comprises KLH. In some embodiments, the antibody-producing cells are isolated, and antibodies derived from the antibody-producing cells are screened for affinity to ifosfamide, and the antibody that binds specifically to ifosfamide is monoclonal. In some embodiments, the method further comprises constructing hybridomas from the isolated antibody-producing cells. In some embodiments, the method further comprises screening nucleic acids from the isolated antibody-producing cells by phage display. In some embodiments, the method further comprises screening for antibodies that bind specifically to ifosfamide compared to an acyclic metabolite of formula (III). In some embodiments, the antibodies from the host organism are screened for affinity to ifosfamide, and the antibody that binds specifically to ifosfamide is polyclonal.

DETAILED DESCRIPTION OF THE EMBODIMENTS

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there is a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, "amine" or "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl. A non-limiting example includes free amino (i.e., —$NH_2$).

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "carboxylic acid" refers to a "—(C=O)—OH" group.

As used herein, "hydrazide" refers to a "—(C=O)—NH—$NH_2$" group.

As used herein, "hydrazine" refers to a "—NH—$NH_2$" group.

As used herein, "oxime" refers to a "—RC=N—OH" group, in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocycle.

As used herein, "thiol" refers to a "—SH" group.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocylyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "cyano" group refers to a "—CN" group.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$, alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein.

The terms "immunogen" and "immunogenic" refer to substances capable of eliciting, producing, or generating an immune response in an organism.

The term "conjugate" refers to any substance formed from the joining together of two parts. Representative conjugates in accordance with some embodiments herein include those formed by the joining together of a small molecule, such as the compound of Formula (I) or (II), and a large molecule, such as a carrier or a polyamine polymer, particularly protein. In the conjugate the small molecule may be joined at one or more active sites on the large molecule.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

An "immunogenic carrier," as used herein, is an immunogenic substance, commonly a protein, that can join with a hapten, thereby enabling these hapten derivatives to induce an immune response and elicit the production of antibodies that can bind specifically with these haptens. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized. In some embodiments, KLH is used as an immunogenic carrier.

Immunogenic carriers can also include poly amino-polysaccharides, which are high molecular weight polymers built up by repeated condensations of monosaccharides. Examples of polysaccharides are starches, glycogen, cellulose, carbohydrate gums such as gum arabic, agar, and so forth. The polysaccharides may also contain polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter.

Cyclophosphamide Analogs

Some embodiments of the present application are directed to a cyclophosphamide analog comprising a structure of Formula (I) or (II):

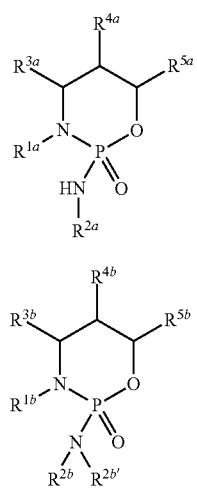

wherein $R^{1a}$ is selected from hydrogen or —$(CH_2)_m$—X;
$R^{2a}$ is —$(CH_2)_n$—Y;
$R^{1b}$ is —$(CH_2)_m$—X;
each of $R^{2b}$ and $R^{2b'}$ is independently selected from is —$(C_2)_k$—Z;
each $R^{3a}$, $R^{4a}$, $R^{5a}$, $R^{3b}$, $R^{4b}$ and $R^{5b}$ is independently selected from hydrogen, halogen, hydroxy, amino, cyano, $C_1$-$C_6$ alkyl, $C_2$-$C_6$ alkenyl, $C_2$-$C_6$ alkynyl, $C_3$-$C_7$ cycloalkyl, 5-10 membered heterocyclyl, aryl, aralkyl, 5-10 membered heteroaryl, $C_1$-$C_6$ alkoxy, $C_1$-$C_6$ alkoxy($C_1$-$C_6$)alkyl, aryloxy, halo($C_1$-$C_6$)alkyl, halo($C_1$-$C_6$)alkoxy, $C_1$-$C_6$ alkylthio, arylthio, amino ($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, and oxo (=O);
X is a functional group selected from amine, thiol, carboxylic acid, hydrazide, hydrazine, oxime, or hydroxylamine;
Y is a functional group independently selected from halogen, hydroxy, amine, thiol, carboxylic acid, hydrazide, hydrazine, oxime, or hydroxylamine;
Z is selected from halogen or hydroxy; and
each m, n and k is independently an integer from 2 to 10.

In some embodiments of the compounds of Formula (I), $R^{1a}$ is hydrogen and $R^{2a}$ is —$(CH_2)_n$—Y. In some such embodiments, Y is a functional group selected from amine, thiol, carboxylic acid, hydrazide, hydrazine, oxime, or hydroxylamine. In one embodiment, Y is thiol. In another embodiment, Y is carboxylic acid.

In some embodiments of the compounds of Formula (I), $R^{1a}$ is —$(CH_2)_m$—X and X is selected from amine, thiol, carboxylic acid, hydrazide, hydrazine, oxime, or hydroxylamine. In one embodiment, X is thiol. In another embodiment, X is carboxylic acid In some such embodiments, $R^{2a}$ is —$(CH_2)_n$—Y and Y is selected from chloride or hydroxy.

In some embodiments of the compounds of Formula (II), $R^{1b}$ is —$(CH_2)_m$—X and X is a functional group selected from amine, thiol, carboxylic acid, hydrazide, hydrazine, oxime, or hydroxylamine. In one embodiment, Y is thiol. In another embodiment, Y is carboxylic acid. In some such embodiments, each $R^{2b}$ and $R^{2b'}$ is —$(CH_2)_k$—Z and Z is selected from chloride or hydroxy.

In some embodiments of the compounds of Formula (I) or (II), m is an integer of 2. In some other embodiments, m is an integer of 3.

In some embodiments of the compounds of Formula (I) or (II), n is an integer of 2.

In some embodiments of the compounds of Formula (I) or (II), k is an integer of 2.

In some embodiments of the compounds of Formula (I) or (II), each of the linker group —$(CH_2)_m$—, —$(CH_2)_n$—, —$(CH_2)_k$— may be optionally substituted. Alternatively, one or more carbon atoms can be replaced with one or more heteroatoms, such as O, S, or N.

In some embodiments of the compounds of Formula (I) or (II), at least one of $R^{3a}$, $R^{4a}$, $R^{5a}$, $R^{3b}$, $R^{4b}$ and $R^{5b}$ is hydrogen. In some preferred embodiments, each of $R^{3a}$, $R^{4a}$, $R^{5a}$, $R^{3b}$, $R^{4b}$ and $R^{5b}$ is hydrogen and the Formulae (I) and (II) are represented by Formulae (Ia) an (IIa):

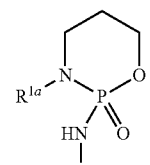

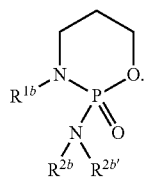

Antibodies

Some embodiments include antibodies, and/or methods of making antibodies. As used herein, "antibody" refers to full-size antibodies, and unless stated otherwise, antigen-binding fragments thereof. Antigen-binding fragments of antibodies can be formatted into a variety of protein formats according to embodiments herein. Antigen-binding fragments of antibodies, or "antibody fragments" as used herein include a portion of an intact antibody comprising the antigen binding site or variable region of the intact antibody. Some antibody fragments are free of the constant heavy chain domains (i.e. $C_{H2}$, $C_{H3}$, and H4, depending on antibody isotype) of the Fc region of the intact antibody, or a portion thereof. Examples of antibody fragments include, but are not limited to Fab, Fab', Fab'-SH, F(ab').sub.2, and Fv fragments; minibodies; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments, for example bispecific antibodies. In some embodiments, the antibody is monoclonal. In some embodiments, the antibody is chimeric. In some embodiments, the antibody is murine. In some embodiments, the antibody is rabbit. In some embodiments, the antibody is rat. In some embodiments, the antibody is goat. In some embodiments, the antibody is guinea pig. In some embodiments, the antibody is donkey. In some embodiments, the antibody is humanized. In some embodiments, the antibody is human.

Antibodies can be produced under in vivo, ex vivo, and/or in vitro conditions. The general structure of antibodies has been described, for example, in U.S. Pat. No. 6,156,878, which is hereby incorporated by reference for its disclosure of antibody structure and for all purposes. Naturally-occurring antibodies or immunoglobulins are typically tetramers of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, can bind antigen. Antibodies, fragments of antibodies, and individual chains are also referred to herein as immunoglobulins.

A normal naturally-occurring antibody heavy or light chain has an N-terminal ($NH_2$) variable (V) region and a C-terminal (—COOH) constant (C) region. The heavy chain variable region is referred to as $V_H$ (including, for example, $V_{gamma}$), and the light chain variable region is referred to as $V_L$ (including $V_{kappa}$ or $V_{lambda}$). The variable region is the part of the molecule that binds to the antibody's cognate antigen, while the Fc region (the second and third domains of the C region) determines the antibody's effector function (e.g., complement fixation). Full-length immunoglobulin or antibody "light chains" (generally about 25 kDa, about 214 amino acids) are encoded by a variable region gene at the N-terminus (generally about 110 amino acids) and a kappa or lambda constant region gene at the COOH-terminus. Full-length immunoglobulin or antibody "heavy chains" (generally about 50 kDa, about 446 amino acids), are similarly encoded by a variable region gene (generally encoding about 116 amino acids) and one of the constant region genes, e.g., gamma (encoding about 330 amino acids). Typically, the "$V_L$" will include the portion of the light chain encoded by the $V_L$ and/or $J_L$ (J or joining region) gene segments, and the "$V_H$" will include the portion of the heavy chain encoded by the $V_H$ and/or $D_H$ (D or diversity region) and $J_H$ gene segments. See, generally, Roitt et al., Immunology (2d ed. 1989), Chapter 6 and Paul, Fundamental Immunology (Raven Press, 2d ed., 1989) (each of which is incorporated by reference for all purposes).

An immunoglobulin light or heavy chain variable region consists of a "framework" region ("FR," which also may be referred to herein as "FWR") interrupted by three hypervariable regions, also called complementarity-determining regions or CDRs. The CDRs are typically referred to as CDR1, CDR2, and CDR3, numbered sequentially starting from the N-terminus. From N-terminal to C-terminal, both light and heavy chains include domains FR1, CDR1, FR2, CDR2, FR3, CDR3 and FR4. Domains of the heavy chain may be referred to herein as HFR1, HCDR1, HFR2, HCDR2, HFR3, HCDR3, and HFR4. Domains of the light chain may be referred to herein as LFR1, LCDR1, LFR2, LCDR2, LHFR3, LCDR3, and LFR4. The extent of the framework region and CDRs have been defined (see Kabat et al. (1987), "Sequences of Proteins of Immunological Interest," U.S. Department of Health and Human Services; Chothia et al., J. Mol. Biol. 196:901-917 (1987) (each of which is incorporated by reference herein for all purposes). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen.

The constant region of the heavy chain molecule, also known as $C_H$, determines the isotype of the antibody. Antibodies are referred to as IgM, IgD, IgG, IgA, and IgE depending on the heavy chain isotype. The isotypes are encoded in the mu, delta, gamma, alpha, and epsilon segments of the heavy chain constant region, respectively. In addition, there are a number of gamma subtypes. There are two types of light chains, kappa and lambda. The determinants of these subtypes typically reside in the constant region of the light chain, also referred to as the $C_L$ in general, and $C_{kappa}$ or $C_{lambda}$ in particular.

The heavy chain isotypes can determine different effector functions of the antibody, such as opsonization or complement fixation. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form. In some embodiments, an antibody as described herein, for example a monoclonal antibody, has an IgG1, IgG2, IgG3, IgG4, IgD, IgE, or IgM isotype.

As used herein, the terms, "specifically," "selectively," and the like, including variations of these root terms refer to an antibody that binds with a higher degree to the indicated epitope than at least one other substance to which the antibody is exposed. For example, in some embodiments, the antibody can bind specifically to cyclophosphamide or ifosfamide, but not to an acyclic metabolite thereof. In some embodiments, the antibody binds selectively to cyclophosphamide or ifosfamide as described herein with a $K_d$ numerically less than about $10^{-6}$ M (in which a lower $K_d$ indicates tighter binding), for example, less than about $10^{-6}$ M, $5\times10^{-7}$ M, $10^{-7}$ M, $10^{-8}$ M, $10^{-9}$ M, $10^{-10}$ M, $10^{-11}$ M, $10^{-12}$ M, $5\times10^{-13}$ M, or $10^{-13}$ M, including ranges between any two of the listed values, for example, $10^{-6}$ M to $10^{-13}$ M, $10^{-6}$ M to $5\times10^{-13}$ M, $10^{-7}$ M to $10^{-13}$ M, $10^{-7}$ M to $5\times10^{-13}$ M, $10^{-8}$ M to $10^{-13}$ M, $10^{-8}$ M to $5\times10^{-13}$ M, $10^{-9}$ M to $10^{-13}$ M, or $10^{-9}$ M to $5\times10^{-13}$ M. In some embodiments, the antibody binds to cyclophosphamide or ifosfamide with a $K_d$ numerically less than about $10^{-6}$ M as described herein, and also binds to a conjugate of Formula (I) or Formula (II) as described herein. In some embodiments, the antibody specifically binds to cyclophosphamide with a $K_d$ numerically less than about $10^{-6}$ M, for example less than about $10^{-6}$ M, $5\times10^{-7}$ M, $10^{-7}$ M, $10^{-8}$ M, $10^{-9}$ M, $10^{-10}$ M, $10^{-11}$ M, $10^{-12}$ M, $5\times10^{-13}$ M, or $10^{-13}$ M, including ranges between any two of the listed values and also binds to a conjugate of Formula (I) or Formula (II) as described herein with $K_d$ numerically less than about $10^{-6}$ M.

In some embodiments, the antibody binds specifically to cyclophosphamide with a stronger dissociation coefficient ($K_d$) than to an acyclic metabolite of cyclophosphamide, in which the $K_d$ for cyclophosphamide is numerically less than about $\frac{1}{10}$ the $K_d$ for an acyclic metabolite of cyclophosphamide, for example less than $\frac{1}{10}$, $\frac{1}{20}$, $\frac{1}{50}$, $\frac{1}{100}$, $\frac{1}{500}$, $\frac{1}{1000}$, $\frac{1}{5000}$, $\frac{1}{10000}$, $\frac{1}{530000}$, or $\frac{1}{100000}$, including ranges between any two of the listed values. In a preferred embodiment, the acyclic metabolite of cyclophosphamide has the formula (III):

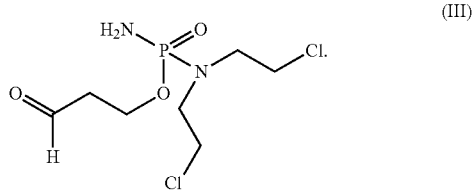 [SMILES: NP(=O)(OCCC=O)N(CCCl)CCCl]

In some embodiments, the antibody further binds to a compound of Formula (I) that comprises a carrier covalently bound to Y as described herein. In some embodiments, the antibody further binds to a compound of Formula (I) that comprises a carrier covalently bound to X as described herein. In some further embodiments, the antibody further binds to a compound of Formula (II) that comprises a carrier covalently bound to X as described herein.

In some embodiments, the antibody binds specifically to ifosfamide with a stronger dissociation coefficient ($K_d$) than to an acyclic metabolite of cyclophosphamide, in which the $K_d$ for ifosfamide is numerically less than about $\frac{1}{10}$ the $K_d$ for an acyclic metabolite of cyclophosphamide, for example less than $\frac{1}{10}$, $\frac{1}{20}$, $\frac{1}{50}$, $\frac{1}{100}$, $\frac{1}{500}$, $\frac{1}{1000}$, $\frac{1}{5000}$, $\frac{1}{10000}$, $\frac{1}{50000}$, or $\frac{1}{100000}$, including ranges between any two of the listed values, and in which the acyclic metabolite of cyclophosphamide has the formula (III). In some embodiments, the antibody further binds to a compound of Formula (I) that comprises a carrier covalently bonded to Y as described herein. In some embodiments, the antibody further binds to a compound of Formula (I) that comprises a carrier covalently bound to X as described herein. In some embodiments, the antibody further binds to a compound of Formula (II) that comprises a carrier covalently bonded to X as described herein.

Immunogen/Assay Conjugate

As discussed above, the functional groups of X or Y of the cyclophosphamide analog of Formula (I) or (II) can covalently bonded to a immunogenic polymer carrier to form an immunogen. Alternatively, these functional groups can covalently bonded to the same polymer or carrier to form a conjugate, except that these polymers or carriers need not produce an immunological response as needed for the immunogen. In one embodiment, X or Y is a carboxylic acid group or active esters thereof that can bond with an amino group of the carrier protein. In another embodiment, X or Y is a thiol group. In some embodiments, the polymer carrier is covalently bound to the cyclophosphamide analog of Formula (I) or Formula (II) by an amide bond. The amide bond can be formed by activating a carboxylic acid moiety of X or Y by reacting the carboxyl group with a leaving group reagent (e.g., N-hydroxysuccinimide, 1-hydroxybenzotriazole, p-nitro phenol and the like). An activating reagent such as dicyclohexylcarbodiimide, diisopropylcarbodiimide, or the like can be used. The activated form of the carboxyl group then can be reacted with a buffered solution containing the polymer carrier, for example a polypeptide. Alternatively, the amide bond can be formed by reacting the amine moiety of X or Y with an activated carboxylic acid moiety of the polymer carrier.

In some embodiments, the polymer carrier is covalently bound to the cyclophosphamide analog of Formula (I) or Formula (II) by a thioether (—S—) bond. The thioether bond can be formed by crosslinking of the thiol moiety of X or Y with an activated or modified amine group of the polymer carrier, for example, those containing maleimide or iodoacetamide moiety. Alternatively, the thioether bond can be formed by reacting the thiol moiety of X or Y with an activated or modified carboxylic acid group of the polymer carrier to form thioester. A typical coupling agent such as N,N'-Dicyclohexylcarbodiimide (DCC) may be used in the reaction. In some embodiments, a polypeptide carrier is covalently bonded to the cyclophosphamide analog of Formula (I) or Formula (II) via a maleimide chemistry, in which one or more lysine residues of the carrier are converted to sulfhydryl-reactive maleimide groups, and the polypeptide carrier is bonded to the cyclophosphamide analog at a sulfhydryl (—SH) group.

Non-limiting exemplary immunogens or conjugates prepared from the cyclophosphamide analogs of Formula (I) are illustrated below:

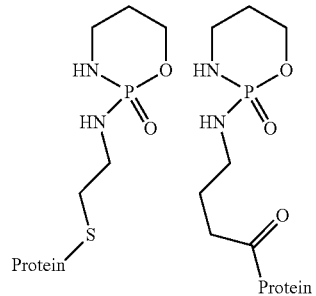

Where, with reference to Formula (I) or (Ia), $R^{1a}$ is hydrogen, and Y (with reference to $R^{2a}$) is thiol or carboxylic acid conjugated with a carrier protein; or

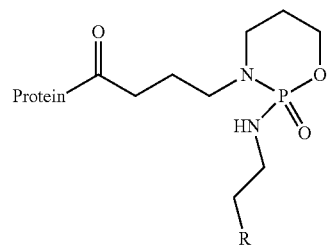

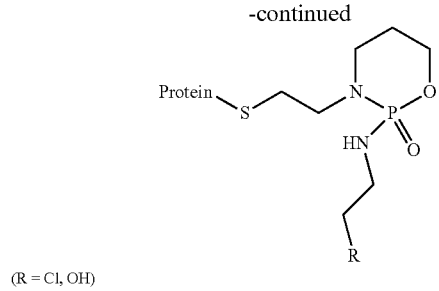

(R = Cl, OH)

Where, with reference to Formula (I) or (Ia), X (with reference to $R^{1a}$) is thiol or carboxylic acid conjugated with a carrier protein, and $R^{2a}$ is —$(CH_2)_2R$ (where R corresponds to Y in the definition of $R^{2a}$ of Formula (I) or (Ia), and R can be selected from chloro or hydroxy).

Furthermore, non-limiting exemplary immunogens or conjugates prepared from the cyclophosphamide analogs of Formula (II) are illustrated below:

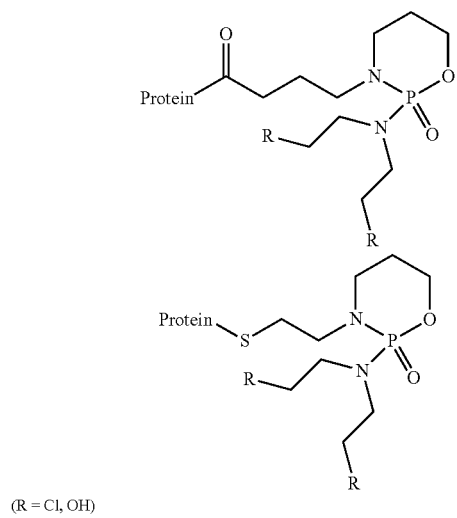

(R = Cl, OH)

Where, with reference to Formula (II) or (IIa), X (with reference to $R^{1b}$) is thiol or carboxylic acid conjugated with a carrier protein, and each $R^{2b}$ and $R^{2b'}$ is independently —$(CH_2)_2R$ (where R corresponds to Z in the definition of $R^{2b}$ and $R^{2b'}$ of Formula (II) or (IIa), and R can be selected from chloro or hydroxy).

In some embodiments, the compound of Formula (I) is conjugated to a carrier comprising, consisting or, or consisting essentially of: an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle (such a compound conjugated to a carrier may also be referred to herein as a "conjugate," including variations of this root term). The carrier can be covalently bonded to either Y or X, as described herein. In some embodiments, the compound of Formula (I) is conjugated to a carrier comprising, consisting or, or consisting essentially of KLH.

In some embodiments, the compound of Formula (II) is conjugated to a carrier comprising, consisting or, or consisting essentially of: an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle (such a compound conjugated to a carrier may also be referred to herein as a "conjugate," including variations of this root term). The carrier can be covalently bound to X. In some embodiments, the compound of Formula (II) is conjugated to a carrier comprising, consisting or, or consisting essentially of KLH.

In some embodiments, the conjugate of the carrier with the compound of Formula (I) or (II), alone or in combination with the antibody generated from the immunogens formed from the immunogenic proteins conjugated with the compound of Formula (I) or (II), can be utilized as immunoassay reagents for determining the presence of cyclophosphamide and/or ifosfamide in a samples.

In addition, assay components of the present application can be provided in a kit. The kit can also contain as an additional reagent and/or additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

Methods of Making Antibodies

In some embodiments, methods of making antibodies that bind to cyclophosphamide or ifosfamide are described. The method can comprise providing an immunogen comprising a compound of Formula (I) or Formula (II) conjugated to a carrier as described herein. The method can comprise immunizing a host organism with the immunogen. The method can comprise isolating antibody-producing cells from the host organism. The method can comprise screening the antibody-producing cells from the host organism for antibodies that binds specifically to a compound of Formula (I) or Formula (II), for example cyclophosphamide or ifosfamide.

Suitable antibodies can be produced using a variety of different techniques. In some embodiments, a non-human host, for example a mouse, rat, guinea pig, rabbit, goat, sheep, donkey, horse, or camel is immunized with antigen such as conjugated cyclophosphamide or ifosfamide as described herein. In some embodiments, the host organism comprises its endogenous immunoglobulin genes. In some embodiments, the host organism is genetically modified so as to comprise one or more immunoglobulin genes of a different organism, for example a human. In some embodiments, the host organisms is genetically modified so as to comprise one or more human immunoglobulin genes, and further does not have any substantial host immunoglobulin gene activity (for example, if the host has had its immunoglobulin genes deleted, transcriptionally silenced, mutated, or otherwise inactivated). In some embodiments, the antigen is delivered at least one of intravenously, subcutaneously or intramuscularly as described herein. In some embodiments, the antigen is delivered on a dosing schedule.

In some embodiments, for example when monoclonal antibodies are of interest, a host animal is immunized with an immunogen as described herein, and antibody-producing cells can be recovered from the host animal, immortalized, and screened for antibodies that specifically bind to the cyclophosphamide or ifosfamide (see, Harlow & Lane, Antibodies, A Laboratory Manual Second Edition (C.S.H.P. NY, 2014), which is hereby incorporated by reference in its entirety. Typically, antibody-producing cells comprise B cells, though another type of antibody-producing cell, the V cell, has also been described in WO 2010/002883 (hereby incorporated by reference in its entirety), and is also contemplated as a suitable antibody-producing cell in some embodiments. In some embodiments, the immunogen comprises the compound of Formula (I) conjugated to a carrier comprising, consisting or, or consisting essentially of: an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle. The carrier can be covalently bound to Y. In some embodiments, the compound of Formula (I) is conjugated to a carrier comprising, consisting or, or consisting essentially of KLH, and is covalently bonded to Y. In some embodiments, the compound of Formula (I) is conjugated to a carrier comprising, consisting or, or consisting essentially of KLH, and is covalently bonded to X. In some embodiments, the immunogen comprises the compound of Formula (II) conjugated to a carrier comprising, consisting or, or consisting essentially of: an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle. The carrier can be covalently bound to X. In some embodiments, the compound of Formula (II) is conjugated to a carrier comprising, consisting or, or consisting essentially of KLH and is covalently bonded to Y. In some embodiments, the host organism is boosted with one or more additional administration of the compound, for example, at least 1, 2, 3, 4, or 5 additional administrations, including ranges between any two of the listed values.

Antibody-producing cells can be harvested from the host organism and isolated using conventional means, for example flow cytometry, or a fluorescence activated cell sorting (FACS™) technique. In some embodiments, the isolated antibody-producing cells are immortalized, as described herein, for example using hybridoma technology. In some embodiments, nucleic acids encoding antibodies are isolated from the antibody-producing cells, and screened for antibodies with suitable affinity to cyclophosphamide and/or ifosfamide.

In some embodiments, the antibody-producing host cells are immortalized using hybridoma technology. Hybridoma techniques are well known in the art. A host animal is typically injected with the antigen, and, after a period of time, antibody-making cell can be isolated, usually from the spleen. The antibody-making cell can be fused with myeloma (or other immortalized cell) cells to provide fused cells, referred to as hybridomas. The hybridomas can be separated from unfused antibody-making cells and myeloma cells. Specific hybridomas can be isolated and tested to confirm that the isolated hybridoma produces antibody specific for the antigen used in the immunization step. The hybridoma so produced combines the ability of the parent antibody-making cell to produce a specific single antibody with the ability of its parent myeloma (or other immortalized) cell to continually grow and divide, either in vitro as a cell culture or in vivo as a tumor after injection into the peritoneal cavity of an animal. Hybridoma lines can be used, for example to produce monoclonal antibodies. Immortalized antibody-producing cells can be screened for antibodies that bind specifically to the cyclophosphamide or ifosfamide as described herein. For example, supernatants from the immortalized antibody-producing cells can be screened for the presence of antibodies that bind to the cyclophosphamide or ifosfamide. In some embodiments, the supernatants are screened using an Enzyme-Linked Immunosorbent Assay (ELISA). For example, the cyclophosphamide or ifosfamide can be immobilized on a substrate, incubated with supernatant from the immortalized antibody-producing cell, the substrate can be washed of the supernatant, and the presence of antibody bound to the immobilized cyclophosphamide or ifosfamide can be detected, for example using a secondary assay. In some embodiments, the supernatants are screened using a no-wash assay. For example, the cyclophosphamide or ifosfamide can be directly or indirectly labeled, for example using a first fluorophore of a FRET pair, contacted with supernatant, and the presence of antibodies bound to the cyclophosphamide or ifosfamide can be detected in solution, for example using a secondary antibody comprising a label such as the second fluorophore of a FRET pair (so as to detect proximity of the secondary antibody to the cyclophosphamide or ifosfamide). In some embodiments, the antibodies are further screened for superior affinity to cyclophosphamide or ifosfamide than an acyclic metabolite thereof, for example an acyclic metabolite of cyclophosphamide of formula (III) (by way of example, a superior affinity can $K_d$ be identified as an affinity to cyclophosphamide of ifosfamide that is numerically less than about $\frac{1}{10}$ than the $K_d$ to the acyclic metabolite).

Another approach in accordance with some embodiments is to isolate nucleic acid sequences, such as DNA sequences or RNA sequences from an antibody-producing cell, and then screening for an antibody having suitable binding characteristics to the cyclophosphamide or ifosfamide as described herein. In some embodiments, the nucleic acids are cloned and, then clones are screened for nucleic acids which encode an antibody having suitable binding characteristics to the cyclophosphamide or ifosfamide as described herein. An example protocol for screening human B cell nucleic acids is described in Huse et al., Science 246:1275-1281 (1989), which is hereby incorporated by reference. In some embodiments, nucleic acids of interest are identified using phage display technology. See, e.g., Dower et al., WO 91/17271 and McCafferty et al., WO 92/010417. Phage display technology can also be used to mutagenize variable regions (or portions thereof such as CDRs) of antibodies previously shown to have affinity for cyclophosphamide or ifosfamide, and screen for antibodies with greater binding affinity. In some embodiments, the nucleic acids are sequenced.

Isolated oligonucleotides encoding a desired antibody of interest can be expressed in an expression system, for example a cellular expression system or a cell-free system. Exemplary cellular expression systems include yeast (e.g., mammalian cells, *E. coli*, insect cells, *Saccharomyces, Pichia*) transformed with recombinant yeast expression vectors containing the nucleotide sequences encoding antibodies; insect cell systems infected with recombinant virus expression vectors (e.g., baculovirus) containing sequences encoding antibodies; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing nucleotide sequences encoding antibodies; mammalian cell systems (e.g., COS, CHO, BHK, 293, 3T3) harboring recombinant expression constructs containing promoters derived from the genome of mammalian cells (e.g., metallothionein promoter) or from mammalian viruses. Exemplary cell free systems include *E. coli* extracts and yeast extracts. The extracts can be lysates. The extracts can be purified, for example, to enrich for ribosomes and/or to remove undesired materials such as debris or host genomic DNA. Nucleic acids encoding antibodies in cell-free systems can include plasmid DNA, linear DNA, or RNA.

In some embodiments, for example when polyclonal antibodies are of interest, a host animal is immunized with an immunogen as described herein, and serum of the host animal is obtained, and polyclonal antibodies against cyclophosphamide or ifosfamide are affinity purified, for example using affinity chromatography. For example, in affinity chromatography, the antigen of interest, such as cyclophosphamide or ifosfamide can be bound to a substrate in a column, and the serum can be passed through the column, so that antibody with affinity to the cyclophosphamide or ifosfamide is immobilized in the column. The column can be washed one or more times to remove non-specific antibody and other substances, and then antibody with affinity to the cyclophosphamide or ifosfamide can be eluted from the column (see, e.g., Harlow & Lane, Antibodies, A Laboratory Manual Second Edition (C.S.H.P NY, 2014).

In addition to the items above, a number of options are set forth herein:

Option 1 comprises a compound comprising a structure of Formula (I) or (II):

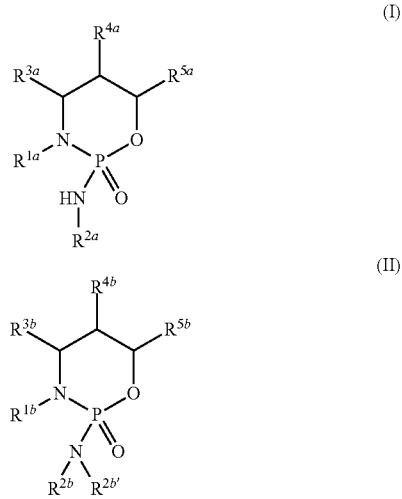

in which $R^{1a}$ is selected from hydrogen or —$(CH_2)_m$—X; $R^{2a}$ is —$(CH_2)_n$—Y; $R^{1b}$ is —$(CH_2)_m$—X; each $R^{2b}$ and $R^{2b'}$ is independently selected from is —$(CH_2)_k$—Z; each $R^{3a}$, $R^{4a}$, $R^{5a}$, $R^{3b}$, $R^{4b}$ and $R^{5b}$ is independently selected from hydrogen, halogen, hydroxy, amino, cyano, $C_1$-$C_6$ alkyl, $C_2$-$C_6$ alkenyl, $C_2$-$C_6$ alkynyl, $C_3$-$C_7$ cycloalkyl, 5-10 membered heterocyclyl, aryl, aralkyl, 5-10 membered heteroaryl, $C_1$-$C_6$ alkoxy, $C_1$-$C_6$ alkoxy($C_1$-$C_6$)alkyl, aryloxy, halo($C_1$-$C_6$)alkyl, halo($C_1$-$C_6$)alkoxy, $C_1$-$C_6$ alkylthio, arylthio, amino ($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, and oxo (=O); X is a functional group selected from amine, thiol, carboxylic acid, hydrazide, hydrazine, oxime, or hydroxylamine; Y is a functional group independently selected from halogen, hydroxy, amine, thiol, carboxylic acid, hydrazide, hydrazine, oxime, or hydroxylamine; Z is selected from halogen or hydroxy; and each m, n and k is independently an integer from 2 to 10. Option 2 comprises the compound of Option 1, wherein $R^{1a}$ is hydrogen. Option 3 comprises the compound of Option 2, wherein Y is selected from amine, thiol, carboxylic acid, hydrazide, hydrazine, oxime, or hydroxylamine. Option 4 comprises the compound of Option 1, wherein $R^{1a}$ is —$(CH_2)_m$—X. Option 5 comprises the compound of Option 4, wherein Y is selected from chloride or hydroxy. Option 6 comprises the compound of Option 1, wherein each $R^{2b}$ and $R^{2b'}$ is —$(CH_2)_k$—Z and Z is selected from chloride or hydroxy. Option 7 comprises the compound of any one of Options 1 to 6, wherein m is an integer of 2. Option 8 comprises the compound of any one of Options 1 to 6, wherein m is an integer of 3. Option 9 comprises the compound of any one of Options 1 to 8, wherein each n and k is an integer of 2. Option 10 comprises the compound of any one of Options 1 to 9, wherein each $R^{3a}$, $R^{4a}$, $R^{5a}$, $R^{3b}$, $R^{4b}$, $R^{5b}$ is hydrogen. Option 11 comprises an immunogen comprising a compound of any one Options 1 to 10 covalently bonded to an immunogenic polymer or carrier through the functional groups X or Y of the compound. Option 12 comprises the immunogen of Option 11, wherein the immunogenic polymer or carrier is selected from an immunologically active protein or polypeptide. Option 13 comprises an antibody which substantially selectively binds to cyclophosphamide and/or ifosfamide. Option 14 comprises the antibody of option 13, wherein said antibody is derived from an immunogen of Options 11 or 12.

Option 15 comprises an immunoassay for detecting in a sample the presence of cyclophosphamide or ifosfamide in a sample, comprising an assay conjugate, wherein said assay conjugate comprising a compound of any one Options 1 to 10 covalently bonded to a carrier through the functional groups X or Y of the compound. Option 16 comprises an immunoassay of Option 15, wherein the carrier is selected from a protein or polypeptide.

Option 17 comprises an immunoassay for detecting in a sample the presence of cyclophosphamide and/or ifosfamide in a sample, comprising the antibody of Option 13 or 14.

Option 18 comprises a kit for detecting the presence of cyclophosphamide and/or ifosfamide in a sample comprising reagents, one of the reagents being a conjugate of a carrier covalently bonded to a compound of any one Options 1 to 10 through the functional groups X or Y of the compound. Option 19 comprises the kit of Option 18, wherein the carrier is selected from a protein or polypeptide. Option 20 comprises the kit of Option 18 or 19, further comprising the antibody of Option 13 or 14. Option 21 comprises the compound of any one of options 1-10, further comprising a carrier covalently bound to X, wherein the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle.

Option 22 comprises the compound of any one of options 1-10 or 21, further comprising a carrier covalently bound to Y, wherein the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle.

Option 23 comprises an antibody that binds specifically to the compound of any one of options 21-22. Option 24 comprises an antibody of option 23, wherein the antibody binds to a cyclic cyclophosphamide with a dissociation constant ($K_d$) that is numerically less than 1/10 the dissociation constant for acyclic cyclophosphamide of formula (III). Option 25 comprises the antibody of option 24, wherein the antibody binds to a cyclic cyclophosphamide with a dissociation constant ($K_d$) that is numerically less than 1/1000 the dissociation constant for acyclic cyclophosphamide of formula (III). Option 26 comprises the antibody of any one of options 23-25, wherein the antibody comprises a monoclonal antibody. Option 27 comprises the antibody of any one of options 23-25, wherein the antibody comprises a polyclonal antibody.

Option 28 comprises a method of making an antibody that binds specifically to cyclophosphamide, the method comprising: administering the immunogen of any of options 11-12 or the compound of any one of options 21-22 to a host organism; isolating antibody-producing cells or antibodies from the host organism; and screening antibodies derived from the antibody-producing cells or the antibodies from the host organism for affinity to cyclophosphamide. Option 29 comprises the method of option 28, wherein the host organism comprises a mouse, rat, hamster, guinea pig, rabbit, donkey, or goat. Option 30 comprises the method of any one of options 28-29, wherein the carrier comprises KLH. Option 31 comprises the method of any one of options 28-29, wherein the antibody-producing cells are isolated, wherein antibodies derived from the antibody-producing cells are screened for affinity to cyclophosphamide, and wherein the antibody that binds specifically to cyclophosphamide is monoclonal. Option 32 comprises the method of option 31, further comprising constructing hybridomas from the isolated antibody-producing cells. Option 33 comprises the method of option 31 or 32, further comprising screening nucleic acids from the isolated antibody-producing cells by phage display. Option 34 comprises the method of any one of options 28-33, further comprising screening for antibodies that bind specifically to cyclophosphamide compared to an acyclic metabolite of formula (III). Option 35 comprises the method of any one of options 31-34, further comprising expressing a nucleic acid encoding the antibody in a host cell. Option 36 comprises the method of any one of options 28-29, wherein the antibodies from the host organism are screened for affinity to cyclophosphamide, and wherein the antibody that binds specifically to cyclophosphamide is polyclonal.

Option 37 comprises the method of making an antibody that binds specifically to ifosfamide, the method comprising: administering the immunogen of any of options 11-12 or the compound of any one of options 21-22 to a host organism; isolating antibody-producing cells or antibodies from the host organism; and screening antibodies derived from the antibody-producing cells or the antibodies from the host organism for affinity to ifosfamide. Option 38 comprises the method of option 37, wherein the host organism comprises a mouse, rat, hamster, guinea pig, rabbit, donkey, or goat. Option 39 comprises the method of any one of options 37-38, wherein the carrier comprises KLH. Option 40 comprises the method of any one of options 37-39, wherein the antibody-producing cells are isolated, wherein antibodies derived from the antibody-producing cells are screened for affinity to ifosfamide, and wherein the antibody that binds specifically to cyclophosphamide is monoclonal. Option 41 comprises the method of option 40, further comprising constructing hybridomas from the isolated antibody-producing cells. Option 42 comprises the method of option 40 or 41, further comprising screening nucleic acids from the isolated antibody-producing cells by phage display. Option 43 comprises the method of any one of options 37-42, further comprising screening for antibodies that bind specifically to cyclophosphamide compared to an acyclic metabolite of formula (III). Option 44 comprises the method of any one of options 40-43, further comprising expressing a nucleic acid encoding the antibody in a host cell. Option 45 comprises the method of any one of options 37-39, wherein the antibodies from the host organism are screened for affinity to cyclophosphamide, and wherein the antibody that binds specifically to cyclophosphamide is polyclonal.

Example I

A compound of Formula (II), in which X is covalently bonded to KLH is synthesized, to prepare a conjugate, as shown:

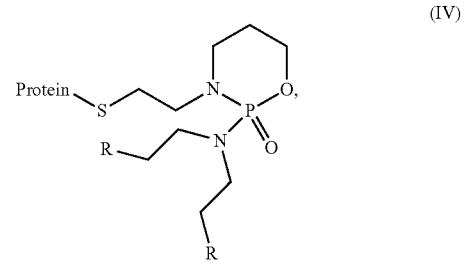

(IV)

in which the protein is KLH. In particular, a maleimide-activated KLH protein is covalently bonded to the thiol group of $R^{1b}$ to form the conjugate shown in Formula (IV) in which the "protein" comprises KLH.

The conjugate is injected into a BALB/c mouse host by intramuscular injection, and incubated for 5 days, and then the mouse host is boosted by a second administration of the conjugate. B cells are harvested from the mouse host, and B cell clones are fused with myeloma cells to construct hybridomas. Hybridomas are cultured, and supernatants are collected. The supernatants are screened using an ELISA assay to identify hybridomas with affinity to ifosfamide. Those hybridomas are expanded, and DNAs coding antibody variable regions are sequenced so as to obtain the variable region sequences of monoclonal antibodies with affinity to cyclophosphamide. Monoclonal antibodies are constructed, and are further screened for specificity to cyclophosphamide over the acyclic metabolite of formula (III).

Example II

A compound of Formula (I), in which Y is covalently bound to human serum albumin via a thiol-selective coupling reaction, to prepare a conjugate, as shown:

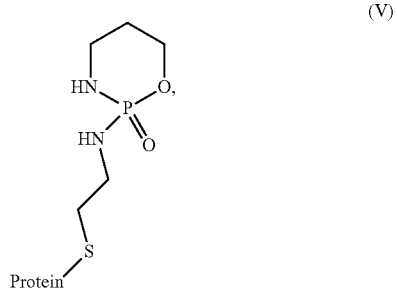

(V)

in which the protein is human serum albumin.

The conjugate is injected into a rabbit host by intramuscular injection, and incubated for 7 days, and then the rabbit host is boosted by a second administration of the conjugate. Immune serum from the rabbit is then collected. The serum is affinity purified for immunoglobulins that bind specifically to ifosfamide using affinity chromatography in which ifosfamide is immobilized on the solid phase. The column is washed, and then antibody with affinity to ifosfamide is eluted from the column, so as to obtain polyclonal antibody with affinity to ifosfamide.

What is claimed is:

1. A compound comprising a structure of Formula (I):

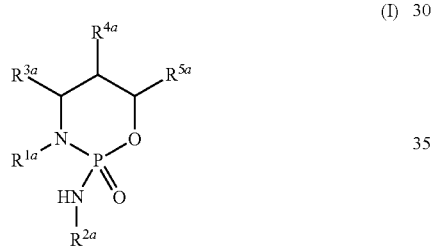

(I)

wherein $R^{1a}$ is selected from hydrogen or —$(CH_2)_m$—X; $R^{2a}$ is —$(CH_2)_n$—Y;
each $R^{3a}$, $R^{4a}$, $R^{5a}$, $R^{3b}$, $R^{4b}$ and $R^{5b}$ is independently selected from hydrogen, halogen, hydroxy, amino, cyano, $C_1$-$C_6$ alkyl, $C_2$-$C_6$ alkenyl, $C_2$-$C_6$ alkynyl, $C_3$-$C_7$ cycloalkyl, 5-10 membered heterocyclyl, aryl, aralkyl, 5-10 membered heteroaryl, $C_1$-$C_6$ alkoxy, $C_1$-$C_6$ alkoxy($C_1$-$C_6$)alkyl, aryloxy, halo($C_1$-$C_6$)alkyl, halo($C_1$-$C_6$)alkoxy, $C_1$-$C_6$ alkylthio, arylthio, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, and oxo (=O);
X is a functional group selected from amine, thiol, carboxylic acid, hydrazide, hydrazine, oxime, or hydroxylamine;
Y is a functional group independently selected from hydroxy, amine, thiol, carboxylic acid, hydrazide, hydrazine, oxime, or hydroxylamine;
Z is selected from halogen or hydroxy; and
each m, n and k is independently an integer from 2 to 10.

2. The compound of claim 1, wherein $R^{1a}$ is hydrogen.

3. The compound of claim 2, wherein Y is selected from amine, thiol, carboxylic acid, hydrazide, hydrazine, oxime, or hydroxylamine.

4. The compound of claim 1, wherein $R^{1a}$ is —$(CH_2)_m$—X.

5. The compound of claim 4, wherein Y is hydroxy.

6. The compound of claim 1, wherein m is an integer of 2.

7. An immunogen comprising a compound of claim 1 covalently bonded to an immunogenic polymer or carrier through the functional groups X or Y of the compound.

8. The immunogen of claim 7, wherein the immunogenic polymer or carrier is selected from an immunologically active protein or polypeptide.

9. A kit for detecting the presence of cyclophosphamide and/or ifosfamide in a sample comprising reagents, one of the reagents being a conjugate of a carrier covalently bonded to a compound of claim 1 through the functional groups X or Y of the compound.

10. The compound of claim 1, further comprising a carrier covalently bound to X, wherein the carrier comprises at least one of an albumin or fragment thereof, a serum protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle.

11. The compound of claim 1, further comprising a carrier covalently bound to Y, wherein the carrier comprises at least one of an albumin or fragment thereof, a serum Protein, a lipoprotein, bovine serum albumin (BSA), keyhole limpet hemocyanin (KLH), egg ovalbumin, bovine thyroglobulin (BTG), a synthetic poly(amino acids), a poly amino-polysaccharide, a poly nucleic acid, a poly amino acid, a polysaccharide, or a solid particle.

12. A method of making an antibody that binds specifically to cyclophosphamide, the method comprising:
administering the immunogen of claim 7 to a host organism;
isolating antibody-producing cells or antibodies from the host organism; and
screening antibodies derived from the antibody-producing cells or the antibodies from the host organism for affinity to cyclophosphamide.

13. The method of claim 12, wherein the antibody-producing cells are isolated, wherein antibodies derived from the antibody-producing cells are screened for affinity to cyclophosphamide, and wherein the antibody that binds specifically to cyclophosphamide is monoclonal.

14. The method of claim 12, further comprising screening for antibodies that bind specifically to cyclophosphamide compared to an acyclic metabolite of formula (III)

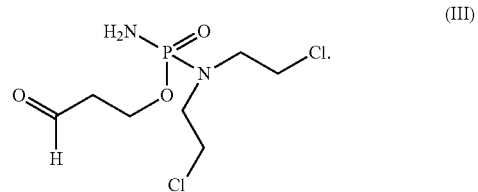 [SMILES: NP(=O)(OCCC=O)N(CCCl)CCCl]

(III)

15. The method of claim 12, wherein the antibodies from the host organism are screened for affinity to cyclophosphamide, and wherein the antibody that binds specifically to cyclophosphamide is polyclonal.

16. A method of making an antibody that binds specifically to ifosfamide, the method comprising:
administering the immunogen of claim 7 to a host organism;

isolating antibody-producing cells or antibodies from the host organism; and screening antibodies derived from the antibody-producing cells or the antibodies from the host organism for affinity to ifosfamide.

17. The method of claim 16, wherein the antibody-producing cells are isolated, wherein antibodies derived from the antibody-producing cells are screened for affinity to ifosfamide, and wherein the antibody that binds specifically to ifosfamide is monoclonal.

18. The method of claim 16, further comprising screening for antibodies that bind specifically to ifosfamide compared to an acyclic metabolite of formula (III).

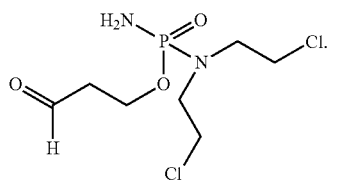

(III)

19. The method of claim 16, wherein the antibodies from the host organism are screened for affinity to ifosfamide, and wherein the antibody that binds specifically to ifosfamide is polyclonal.

\* \* \* \* \*